United States Patent
Sowards et al.

(10) Patent No.: US 12,287,403 B2
(45) Date of Patent: Apr. 29, 2025

(54) ULTRASOUND IMAGING SYSTEM HAVING NEAR-INFRARED/INFRARED DETECTION

(71) Applicant: Bard Access Systems, Inc., Salt Lake City, UT (US)

(72) Inventors: Steffan Sowards, Salt Lake City, UT (US); William Robert McLaughlin, Bountiful, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 30 days.

(21) Appl. No.: 17/722,111

(22) Filed: Apr. 15, 2022

(65) Prior Publication Data
US 2022/0334251 A1    Oct. 20, 2022

Related U.S. Application Data

(60) Provisional application No. 63/175,475, filed on Apr. 15, 2021.

(51) Int. Cl.
*G01S 15/89* (2006.01)
*G01S 15/86* (2020.01)
(Continued)

(52) U.S. Cl.
CPC .......... *G01S 15/8906* (2013.01); *G01S 15/86* (2020.01); *G01S 17/89* (2013.01); *G06T 7/0014* (2013.01);
(Continued)

(58) Field of Classification Search
CPC ...... G01S 17/89; G01S 15/8906; G01S 15/86; A61B 5/0086; A61B 8/085; A61B 5/489;
(Continued)

(56) References Cited

U.S. PATENT DOCUMENTS 3,697,917 A    10/1972  Orth et al.
5,148,809 A    9/1992   Biegeleisen-Knight et al.
(Continued)

FOREIGN PATENT DOCUMENTS

CN    102871645 A      1/2013
CN    105107067 A   *  12/2015
(Continued)

OTHER PUBLICATIONS

PCT/US2022/049983 filed Nov. 15, 2022 International Search Report and Written Opinion dated Mar. 29, 2023.
(Continued)

*Primary Examiner* — Daniel L Murphy
*Assistant Examiner* — Amie M Ndure
(74) *Attorney, Agent, or Firm* — Rutan & Tucker LLP

(57) ABSTRACT

Disclosed herein is an ultrasound imaging system including an ultrasound probe and a blood vessel visualization device. The ultrasound probe includes an ultrasound generation device and is configured to detect one or more blood vessels. The blood vessel visualization device is configured to project a depiction of the blood vessel topography within a target area. The blood vessel visualization device can include one or more near-infrared/infrared emitters configured to generate infrared/near-infrared waves within the target area, one or more near-infrared/infrared sensors configured to detect the difference in reflective properties of tissue and blood vessels within the target area, and one or more visual light projectors configured to project a blood vessel visualization depiction of the blood vessel topography onto the target area.

16 Claims, 5 Drawing Sheets

(51) Int. Cl.
*G01S 17/89* (2020.01)
*G06T 7/00* (2017.01)

(52) U.S. Cl.
CPC ............. *G06T 2207/10048* (2013.01); *G06T 2207/10132* (2013.01); *G06T 2207/30101* (2013.01)

(58) Field of Classification Search
CPC ... A61B 5/02007; A61B 8/461; A61B 8/5261; A61B 8/0891; A61B 8/463; A61B 8/4472; A61B 8/4444; A61B 8/46; A61B 8/54; G06T 7/0014; G16H 30/40; G16H 40/63
See application file for complete search history.

(56) References Cited

U.S. PATENT DOCUMENTS

| | | |
|---|---|---|
| 5,181,513 A | 1/1993 | Touboul et al. |
| 5,325,293 A | 6/1994 | Dorne |
| 5,349,865 A | 9/1994 | Kavli et al. |
| 5,441,052 A | 8/1995 | Miyajima |
| 5,549,554 A | 8/1996 | Miraki |
| 5,573,529 A | 11/1996 | Haak et al. |
| 5,758,650 A | 6/1998 | Miller et al. |
| 5,775,322 A | 7/1998 | Silverstein et al. |
| 5,879,297 A | 3/1999 | Haynor et al. |
| 5,897,503 A | 4/1999 | Lyon et al. |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,074,367 A | 6/2000 | Hubbell |
| 6,129,668 A | 10/2000 | Haynor et al. |
| 6,132,379 A | 10/2000 | Patacsil et al. |
| 6,216,028 B1 | 4/2001 | Haynor et al. |
| 6,233,476 B1 | 5/2001 | Strommer et al. |
| 6,245,018 B1 | 6/2001 | Lee |
| 6,263,230 B1 | 7/2001 | Haynor et al. |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,543,642 B1 | 4/2003 | Milliorn |
| 6,554,771 B1 | 4/2003 | Buil et al. |
| 6,592,520 B1 | 7/2003 | Peszynski et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,733,458 B1 | 5/2004 | Steins et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,840,379 B2 | 1/2005 | Franks-Farah et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Ying et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,038,619 B2 | 10/2011 | Steinbacher |
| 8,060,181 B2 | 11/2011 | Rodriguez Ponce et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,336,536 B1 | 12/2012 | Wood-Putnam et al. |
| 8,388,541 B2 | 3/2013 | Messerly et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,781,555 B2 | 7/2014 | Burnside et al. |
| 8,790,263 B2 | 7/2014 | Randall et al. |
| 8,849,382 B2 | 9/2014 | Cox et al. |
| 8,939,908 B2 | 1/2015 | Suzuki et al. |
| 8,961,420 B2 | 2/2015 | Zhang |
| 9,022,940 B2 | 5/2015 | Meier |
| 9,087,147 B1 | 7/2015 | Fonte |
| 9,138,290 B2 | 9/2015 | Hadjicostis |
| 9,199,082 B1 | 12/2015 | Yared et al. |
| 9,204,858 B2 | 12/2015 | Pelissier et al. |
| 9,220,477 B2 | 12/2015 | Urabe et al. |
| 9,295,447 B2 | 3/2016 | Shah |
| 9,320,493 B2 | 4/2016 | Visveshwara |
| 9,357,980 B2 | 6/2016 | Toji et al. |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,582,876 B2 | 2/2017 | Specht |
| 9,610,061 B2 | 4/2017 | Ebbini et al. |
| 9,636,031 B2 | 5/2017 | Cox |
| 9,649,037 B2 | 5/2017 | Lowe et al. |
| 9,649,048 B2 | 5/2017 | Cox et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 10,043,272 B2 | 8/2018 | Forzoni et al. |
| 10,449,330 B2 | 10/2019 | Newman et al. |
| 10,524,691 B2 | 1/2020 | Newman et al. |
| 10,751,509 B2 | 8/2020 | Misener |

(56) References Cited

U.S. PATENT DOCUMENTS

| | | |
|---|---|---|
| 11,564,861 B1 | 1/2023 | Gaines |
| 11,900,593 B2 | 2/2024 | Dhatt et al. |
| 2002/0038088 A1 | 3/2002 | Imran et al. |
| 2003/0047126 A1 | 3/2003 | Tomaschko |
| 2003/0106825 A1 | 6/2003 | Molina et al. |
| 2003/0120154 A1 | 6/2003 | Sauer et al. |
| 2003/0125629 A1 | 7/2003 | Ustuner |
| 2003/0135115 A1 | 7/2003 | Burdette et al. |
| 2003/0149366 A1 | 8/2003 | Stringer et al. |
| 2004/0015080 A1 | 1/2004 | Kelly et al. |
| 2004/0055925 A1 | 3/2004 | Franks-Farah et al. |
| 2004/0197267 A1 | 10/2004 | Black et al. |
| 2005/0000975 A1 | 1/2005 | Carco et al. |
| 2005/0049504 A1 | 3/2005 | Lo et al. |
| 2005/0075597 A1 | 4/2005 | Vournakis et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0004290 A1 | 1/2006 | Smith et al. |
| 2006/0013523 A1 | 1/2006 | Childlers et al. |
| 2006/0015039 A1 | 1/2006 | Cassidy et al. |
| 2006/0020204 A1 | 1/2006 | Serra et al. |
| 2006/0047617 A1 | 3/2006 | Bacioiu et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2006/0241463 A1 | 10/2006 | Shau et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0167738 A1 | 7/2007 | Timinger et al. |
| 2007/0199848 A1 | 8/2007 | Ellswood et al. |
| 2007/0239005 A1 | 10/2007 | Ogasawara |
| 2007/0239120 A1 | 10/2007 | Brock et al. |
| 2007/0249911 A1 | 10/2007 | Simon |
| 2007/0287886 A1 | 12/2007 | Saadat |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0108930 A1 | 5/2008 | Weitzel et al. |
| 2008/0125651 A1 | 5/2008 | Watanabe et al. |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0269605 A1 | 10/2008 | Nakaya |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0012401 A1 | 1/2009 | Steinbacher |
| 2009/0074280 A1 | 3/2009 | Lu et al. |
| 2009/0124903 A1 | 5/2009 | Osaka |
| 2009/0137887 A1 | 5/2009 | Shariati et al. |
| 2009/0137907 A1 | 5/2009 | Takimoto et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0281413 A1 | 11/2009 | Boyden et al. |
| 2009/0306509 A1 | 12/2009 | Pedersen et al. |
| 2010/0010348 A1 | 1/2010 | Halmann |
| 2010/0168576 A1 | 7/2010 | Poland et al. |
| 2010/0211026 A2 | 8/2010 | Sheetz et al. |
| 2010/0249598 A1 | 9/2010 | Smith et al. |
| 2010/0286515 A1 | 11/2010 | Gravenstein et al. |
| 2010/0312121 A1 | 12/2010 | Guan |
| 2010/0324423 A1 | 12/2010 | El-Aklouk et al. |
| 2011/0002518 A1 | 1/2011 | Ziv-Ari et al. |
| 2011/0026796 A1 | 2/2011 | Hyun et al. |
| 2011/0071404 A1 | 3/2011 | Schmitt et al. |
| 2011/0074244 A1 | 3/2011 | Osawa |
| 2011/0087107 A1 | 4/2011 | Lindekugel et al. |
| 2011/0166451 A1 | 7/2011 | Blaivas et al. |
| 2011/0282188 A1 | 11/2011 | Burnside et al. |
| 2011/0295108 A1 | 12/2011 | Cox et al. |
| 2011/0313293 A1 | 12/2011 | Lindekugel et al. |
| 2012/0136242 A1 | 5/2012 | Qi et al. |
| 2012/0136256 A1 | 5/2012 | Nozaki et al. |
| 2012/0165679 A1 | 6/2012 | Orome et al. |
| 2012/0179038 A1 | 7/2012 | Meurer et al. |
| 2012/0179042 A1 | 7/2012 | Fukumoto et al. |
| 2012/0179044 A1 | 7/2012 | Chiang et al. |
| 2012/0197132 A1 | 8/2012 | O'Connor |
| 2012/0220865 A1 | 8/2012 | Brown et al. |
| 2012/0277576 A1 | 11/2012 | Lui |
| 2013/0041250 A1 | 2/2013 | Pelissier et al. |
| 2013/0102889 A1 | 4/2013 | Southard et al. |
| 2013/0131499 A1 | 5/2013 | Chan et al. |
| 2013/0131502 A1 | 5/2013 | Blaivas et al. |
| 2013/0144166 A1 | 6/2013 | Specht et al. |
| 2013/0150724 A1 | 6/2013 | Blaivas et al. |
| 2013/0188832 A1 | 7/2013 | Ma et al. |
| 2013/0197367 A1* | 8/2013 | Smok .......... A61B 8/085 600/454 |
| 2013/0218024 A1 | 8/2013 | Boctor et al. |
| 2013/0323700 A1 | 12/2013 | Samosky et al. |
| 2013/0338503 A1 | 12/2013 | Cohen et al. |
| 2013/0338508 A1 | 12/2013 | Nakamura et al. |
| 2013/0345566 A1 | 12/2013 | Weitzel et al. |
| 2014/0005530 A1 | 1/2014 | Liu et al. |
| 2014/0031694 A1 | 1/2014 | Solek |
| 2014/0066779 A1 | 3/2014 | Nakanishi |
| 2014/0073976 A1 | 3/2014 | Fonte et al. |
| 2014/0100440 A1 | 4/2014 | Cheline et al. |
| 2014/0114194 A1 | 4/2014 | Kanayama et al. |
| 2014/0170620 A1 | 6/2014 | Savitsky et al. |
| 2014/0180098 A1 | 6/2014 | Flaherty et al. |
| 2014/0180116 A1 | 6/2014 | Lindekugel et al. |
| 2014/0188133 A1 | 7/2014 | Misener |
| 2014/0188440 A1 | 7/2014 | Donhowe et al. |
| 2014/0276059 A1 | 9/2014 | Sheehan |
| 2014/0276069 A1 | 9/2014 | Amble et al. |
| 2014/0276081 A1 | 9/2014 | Tegels |
| 2014/0276085 A1 | 9/2014 | Miller |
| 2014/0276690 A1 | 9/2014 | Grace |
| 2014/0296694 A1 | 10/2014 | Jaworski |
| 2014/0343431 A1 | 11/2014 | Vajinepalli et al. |
| 2014/0357994 A1 | 12/2014 | Jin et al. |
| 2015/0005738 A1 | 1/2015 | Blacker |
| 2015/0011887 A1* | 1/2015 | Ahn .......... A61B 8/085 600/454 |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0141821 A1 | 5/2015 | Yoshikawa et al. |
| 2015/0190111 A1 | 7/2015 | Fry |
| 2015/0209003 A1 | 7/2015 | Halmann et al. |
| 2015/0209113 A1 | 7/2015 | Burkholz et al. |
| 2015/0209510 A1 | 7/2015 | Burkholz et al. |
| 2015/0209526 A1 | 7/2015 | Matsubara et al. |
| 2015/0245820 A1 | 9/2015 | Tamada |
| 2015/0257735 A1* | 9/2015 | Ball .......... A61B 8/462 600/443 |
| 2015/0272448 A1 | 10/2015 | Fonte et al. |
| 2015/0282890 A1 | 10/2015 | Cohen et al. |
| 2015/0294497 A1 | 10/2015 | Ng et al. |
| 2015/0297097 A1 | 10/2015 | Matsubara et al. |
| 2015/0342572 A1 | 12/2015 | Tahmasebi Maraghoosh et al. |
| 2015/0359520 A1 | 12/2015 | Shan et al. |
| 2015/0359991 A1 | 12/2015 | Dunbar et al. |
| 2016/0000367 A1 | 1/2016 | Lyon |
| 2016/0000399 A1 | 1/2016 | Halmann et al. |
| 2016/0026894 A1 | 1/2016 | Nagase |
| 2016/0029995 A1 | 2/2016 | Navratil et al. |
| 2016/0038119 A1 | 2/2016 | Desjardins |
| 2016/0081674 A1 | 3/2016 | Bagwan et al. |
| 2016/0113517 A1 | 4/2016 | Lee et al. |
| 2016/0113699 A1 | 4/2016 | Sverdlik et al. |
| 2016/0120607 A1 | 5/2016 | Sorotzkin et al. |
| 2016/0125639 A1 | 5/2016 | Park et al. |
| 2016/0157831 A1 | 6/2016 | Kang et al. |
| 2016/0166232 A1 | 6/2016 | Merritt |
| 2016/0202053 A1 | 7/2016 | Walker et al. |
| 2016/0211045 A1 | 7/2016 | Jeon et al. |
| 2016/0213398 A1 | 7/2016 | Liu |

(56) References Cited

U.S. PATENT DOCUMENTS

| | | |
|---|---|---|
| 2016/0220124 A1 | 8/2016 | Grady et al. |
| 2016/0259992 A1 | 9/2016 | Knodt et al. |
| 2016/0278869 A1 | 9/2016 | Grunwald |
| 2016/0287214 A1 | 10/2016 | Ralovich et al. |
| 2016/0296208 A1 | 10/2016 | Sethuraman et al. |
| 2016/0374644 A1 | 12/2016 | Mauldin, Jr. et al. |
| 2017/0014105 A1 | 1/2017 | Chono |
| 2017/0020561 A1 | 1/2017 | Cox et al. |
| 2017/0079548 A1 | 3/2017 | Silverstein et al. |
| 2017/0086785 A1 | 3/2017 | Bjaerum |
| 2017/0103534 A1 | 4/2017 | Park et al. |
| 2017/0143312 A1 | 5/2017 | Hedlund et al. |
| 2017/0164923 A1 | 6/2017 | Matsumoto |
| 2017/0172666 A1 | 6/2017 | Govari et al. |
| 2017/0215842 A1 | 8/2017 | Ryu et al. |
| 2017/0252004 A1 | 9/2017 | Broad et al. |
| 2017/0258522 A1 | 9/2017 | Goshgarian et al. |
| 2017/0328751 A1 | 11/2017 | Lemke |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0228465 A1* | 8/2018 | Southard .............. A61B 8/4427 |
| 2018/0235649 A1 | 8/2018 | Elkadi |
| 2018/0235709 A1 | 8/2018 | Donhowe et al. |
| 2018/0289927 A1 | 10/2018 | Messerly |
| 2018/0296185 A1 | 10/2018 | Cox et al. |
| 2018/0310955 A1 | 11/2018 | Lindekugel et al. |
| 2018/0333135 A1 | 11/2018 | Kim et al. |
| 2018/0344293 A1 | 12/2018 | Raju et al. |
| 2019/0029636 A1 | 1/2019 | Lee et al. |
| 2019/0060001 A1 | 2/2019 | Kohli et al. |
| 2019/0060014 A1 | 2/2019 | Hazelton et al. |
| 2019/0090855 A1 | 3/2019 | Kobayashi et al. |
| 2019/0125210 A1 | 5/2019 | Govari et al. |
| 2019/0200951 A1 | 7/2019 | Meier |
| 2019/0239848 A1 | 8/2019 | Bedi et al. |
| 2019/0239850 A1 | 8/2019 | Dalvin et al. |
| 2019/0307419 A1 | 10/2019 | Durfee |
| 2019/0307515 A1 | 10/2019 | Naito et al. |
| 2019/0307516 A1 | 10/2019 | Schotzko et al. |
| 2019/0365347 A1* | 12/2019 | Abe .................... A61B 5/0095 |
| 2019/0365348 A1 | 12/2019 | Toume et al. |
| 2019/0365354 A1 | 12/2019 | Du |
| 2020/0069929 A1 | 3/2020 | Mason et al. |
| 2020/0113540 A1 | 4/2020 | Gijsbers et al. |
| 2020/0163654 A1 | 5/2020 | Satir et al. |
| 2020/0200900 A1 | 6/2020 | Asami et al. |
| 2020/0229795 A1 | 7/2020 | Tadross et al. |
| 2020/0230391 A1 | 7/2020 | Burkholz et al. |
| 2020/0237403 A1 | 7/2020 | Southard et al. |
| 2020/0281563 A1 | 9/2020 | Muller et al. |
| 2020/0359990 A1 | 11/2020 | Poland et al. |
| 2020/0390416 A1 | 12/2020 | Swan et al. |
| 2021/0059639 A1 | 3/2021 | Howell |
| 2021/0077058 A1 | 3/2021 | Mashood et al. |
| 2021/0137492 A1* | 5/2021 | Imai .................... A61B 8/4254 |
| 2021/0146167 A1 | 5/2021 | Barthe et al. |
| 2021/0161510 A1 | 6/2021 | Sasaki et al. |
| 2021/0186467 A1 | 6/2021 | Urabe et al. |
| 2021/0212668 A1 | 7/2021 | Li et al. |
| 2021/0267569 A1 | 9/2021 | Yamamoto |
| 2021/0267570 A1 | 9/2021 | Ulman et al. |
| 2021/0295048 A1 | 9/2021 | Buras et al. |
| 2021/0315538 A1 | 10/2021 | Brandl et al. |
| 2021/0373602 A1 | 12/2021 | Min |
| 2021/0378627 A1 | 12/2021 | Yarmush et al. |
| 2022/0019313 A1 | 1/2022 | He et al. |
| 2022/0022969 A1 | 1/2022 | Misener |
| 2022/0039777 A1 | 2/2022 | Durfee |
| 2022/0039829 A1 | 2/2022 | Zijlstra et al. |
| 2022/0071593 A1 | 3/2022 | Tran |
| 2022/0096053 A1 | 3/2022 | Sethuraman et al. |
| 2022/0096797 A1 | 3/2022 | Prince |
| 2022/0104791 A1 | 4/2022 | Matsumoto |
| 2022/0104886 A1 | 4/2022 | Blanchard et al. |
| 2022/0117582 A1 | 4/2022 | McLaughlin et al. |
| 2022/0160434 A1 | 5/2022 | Messerly et al. |
| 2022/0168050 A1 | 6/2022 | Sowards et al. |
| 2022/0172354 A1 | 6/2022 | Misener et al. |
| 2022/0225963 A1 | 7/2022 | Sutton et al. |
| 2022/0296303 A1 | 9/2022 | McLeod et al. |
| 2022/0304652 A1 | 9/2022 | Peterson et al. |
| 2022/0330922 A1 | 10/2022 | Sowards et al. |
| 2022/0361840 A1 | 11/2022 | Matsumoto et al. |
| 2023/0048327 A1 | 2/2023 | Lampe et al. |
| 2023/0107629 A1 | 4/2023 | Sowards et al. |
| 2023/0132148 A1 | 4/2023 | Sowards et al. |
| 2023/0135562 A1 | 5/2023 | Misener et al. |
| 2023/0135757 A1 | 5/2023 | Bauer et al. |
| 2023/0138970 A1 | 5/2023 | Sowards et al. |
| 2023/0148872 A1 | 5/2023 | Sowards et al. |
| 2023/0201539 A1 | 6/2023 | Howell |
| 2023/0277153 A1 | 9/2023 | Sowards et al. |
| 2023/0277154 A1 | 9/2023 | Sowards et al. |
| 2023/0293143 A1 | 9/2023 | Sowards et al. |
| 2023/0338010 A1 | 10/2023 | Sturm |
| 2023/0371928 A1 | 11/2023 | Rajguru et al. |
| 2023/0397900 A1 | 12/2023 | Prince |
| 2024/0065673 A1 | 2/2024 | Sowards et al. |
| 2024/0307024 A1 | 9/2024 | Sowards et al. |
| 2025/0017559 A1 | 1/2025 | Denny et al. |

FOREIGN PATENT DOCUMENTS

| | | | |
|---|---|---|---|
| CN | 105107067 B | 5/2018 | |
| EP | 0933063 A1 | 8/1999 | |
| EP | 1504713 A1 | 2/2005 | |
| EP | 1591074 B1 | 5/2008 | |
| EP | 2823766 A1 | 1/2015 | |
| EP | 3181083 A1 | 6/2017 | |
| EP | 3870059 | 9/2021 | |
| JP | 2000271136 A | 10/2000 | |
| JP | 2007222291 A | 9/2007 | |
| JP | 2014150928 A | 8/2014 | |
| JP | 2018175547 A | 11/2018 | |
| KR | 20180070878 A | 6/2018 | |
| KR | 102176196 B1 | 11/2020 | |
| WO | 2004082749 A2 | 9/2004 | |
| WO | 2007115174 A2 | 10/2007 | |
| WO | 2010029521 A2 | 3/2010 | |
| WO | 2010076808 A1 | 7/2010 | |
| WO | 2013059714 A1 | 4/2013 | |
| WO | 2014/115150 A1 | 7/2014 | |
| WO | 2015/017270 A1 | 2/2015 | |
| WO | 2016/081023 A1 | 5/2016 | |
| WO | 2017096487 A1 | 6/2017 | |
| WO | 2017214428 A1 | 12/2017 | |
| WO | 2018/026878 A1 | 2/2018 | |
| WO | 2018134726 A1 | 7/2018 | |
| WO | 2019/232451 A1 | 12/2019 | |
| WO | 2020/002620 A1 | 1/2020 | |
| WO | 2020/016018 A1 | 1/2020 | |
| WO | 2019/232454 A9 | 2/2020 | |
| WO | 2020/044769 A1 | 3/2020 | |
| WO | 2020083660 A1 | 4/2020 | |
| WO | WO-2020067897 A1 * | 4/2020 | ......... A61B 17/3403 |
| WO | 2020/186198 A1 | 9/2020 | |
| WO | 2021123905 A2 | 6/2021 | |
| WO | 2021198226 A1 | 10/2021 | |
| WO | 2022/072727 A2 | 4/2022 | |
| WO | 2022/081904 A1 | 4/2022 | |
| WO | 2022/119853 A1 | 6/2022 | |
| WO | 2022115479 A1 | 6/2022 | |
| WO | 2022119856 A1 | 6/2022 | |
| WO | 2022221703 A1 | 10/2022 | |
| WO | 2022/221714 A1 | 10/2022 | |
| WO | 2023059512 A1 | 4/2023 | |
| WO | 2023076268 A1 | 5/2023 | |
| WO | 2023081220 A1 | 5/2023 | |
| WO | 2023081223 A1 | 5/2023 | |

(56) References Cited

FOREIGN PATENT DOCUMENTS

| WO | 2023091424 A1 | 5/2023 |
|----|---------------|--------|
| WO | 2023167866 A1 | 9/2023 |
| WO | 2023177718 A1 | 9/2023 |
| WO | 2024044277 A1 | 2/2024 |

OTHER PUBLICATIONS

PCT/US2023/014143 filed Feb. 28, 2023 International Search Report and Written Opinion dated Jun. 12, 2023.
PCT/US2023/015266 filed Mar. 15, 2023 International Search Report and Written Opinion dated May 25, 2023.
Saxena Ashish et al Thermographic venous blood flow characterization with external cooling stimulation Infrared Physics and Technology Elsevier Science GB vol. 90 Feb. 9, 2018 Feb. 9, 2018 pp. 8-19 XP085378852.
U.S. Appl. No. 17/020,476, filed Sep. 14, 2020 Notice of Allowance dated Apr. 28, 2022.
U.S. Appl. No. 17/468,318, filed Sep. 7, 2021 Non-Final Office Action dated Apr. 12, 2023.
U.S. 17/684,180, filed Mar. 1, 2022 Restriction Requirement dated May 19, 2023.
PCT/US2022/025082 filed Apr. 15, 2022 International Search Report and Written Opinion dated Jul. 11, 2022.
PCT/US2022/025097 filed Apr. 15, 2022 International Search Report and Written Opinion dated Jul. 8, 2022.
U.S. Appl. No. 17/020,476, filed Sep. 14, 2020 Advisory Action dated Aug. 19, 2022.
U.S. Appl. No. 17/471,015, filed Sep. 9, 2021 Non-Final Office Action dated Aug. 16, 2022.
PCT/US2022/048716 filed Nov. 2, 2022 International Search Report and Written Opinion dated Feb. 24, 2023.
PCT/US2022/048722 filed Nov. 2, 2022 International Search Report and Written Opinion dated Feb. 24, 2023.
PCT/US2022047727 filed Oct. 25, 2022 International Search Report and Written Opinion dated Jan. 25, 2023.
U.S. Appl. No. 17/020,476, filed Sep. 14, 2020 Final Office Action dated Jan. 5, 2023.
U.S. Appl. No. 17/020,476, filed Sep. 14, 2020 Non-Final Office Action dated Sep. 23, 2022.
U.S. Appl. No. 17/471,015, filed Sep. 9, 2021 Non-Final Office Action dated Mar. 30, 2023.
U.S. Appl. No. 17/534,099, filed Nov. 23, 2021 Non-Final Office Action dated Mar. 31, 2023.
U.S. Appl. No. 17/538,911, filed Nov. 30, 2021 Non-Final Office Action dated Mar. 2, 2023.
EP 20866520.8 filed Apr. 5, 2022 Extended European Search Report dated Aug. 22, 2023.
U.S. Appl. No. 17/468,318, filed Sep. 7, 2021 Final Office Action dated Sep. 8, 2023.
U.S. Appl. No. 17/538,911, filed Nov. 30, 2021 Final Office Action dated Sep. 13, 2023.
U.S. Appl. No. 17/684,180, filed Mar. 1, 2022 Non-Final Office Action dated Jul. 28, 2023.
U.S. Appl. No. 17/722,151, filed Apr. 15, 2022 Non-Final Office Action dated Sep. 7, 2023.
Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).
Pagoulatos, N. et al. "New spatial localizer based on fiber optics with applications in 3D ultrasound imaging" Proceeding of Spie, vol. 3976 (Apr. 18, 2000; Apr. 18, 2000).
PCT/US2021/049294 filed Sep. 7, 2021 International Search Report and Written Opinion dated Dec. 8, 2021.
PCT/US2021/049712 filed Sep. 9, 2021 International Search Report and Written Opinion dated Dec. 14, 2021.
PCT/US2021/060622 filed Nov. 23, 2021 International Search Report and Written Opinion dated Mar. 3, 2022.
PCT/US2021/061267 filed Nov. 30, 2021 International Search Report and Written Opinion dated Mar. 9, 2022.
PCT/US2021/061276 filed Nov. 30, 2021 International Search Report and Written Opinion dated Mar. 9, 2022.
Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docld/1235/file/SebastianVogtDissertation.pdf.
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 11, 2020.
U.S. Appl. No. 15/650,474, filed Jul. 14, 2017 Notice of Allowance dated Mar. 1, 2021.
U.S. Appl. No. 17/020,476, filed Sep. 14, 2020 Final Office Action dated Jun. 9, 2022.
U.S. Appl. No. 17/020,476, filed Sep. 14, 2020 Non-Final Office Action dated Feb. 9, 2022.
William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
M. Ikhsan, K. K. Tan, AS. Putra, C. F. Kong, et al., "Automatic identification of blood vessel cross-section for central venous catheter placement using a cascading classifier," 39th Annual International Conference of the IEEE Engineering in Medicine and Biology Society (EMBC). pp. 1489-1492 (Year: 2017).
PCT/US2022/025097 filed Apr. 15, 2021 International Preliminary Report on Patentability dated Oct. 26, 2023.
PCT/US2023/030970 filed Aug. 23, 2023 International Search Report and Written Opinion dated Oct. 30, 2023.
U.S. Appl. No. 17/468,318, filed Sep. 7, 2021 Advisory Action dated Nov. 6, 2023.
U.S. Appl. No. 17/468,318, filed Sep. 7, 2021 Notice of Allowance dated Jan. 18, 2024.
U.S. Appl. No. 17/471,015, filed Sep. 9, 2021 Advisory Action dated Feb. 2, 2024.
U.S. Appl. No. 17/471,015, filed Sep. 9, 2021 Final Office Action dated Oct. 12, 2023.
U.S. Appl. No. 17/471,015, filed Sep. 9, 2021 Non-Final Office Action dated Mar. 28, 2024.
U.S. Appl. No. 17/534,099, filed Nov. 23, 2021 Advisory Action dated Dec. 8, 2023.
U.S. Appl. No. 17/534,099, filed Nov. 23, 2021 Final Office Action dated Sep. 29, 2023.
U.S. Appl. No. 17/534,099, filed Nov. 23, 2021 Non-Final Office Action dated Mar. 14, 2024.
U.S. Appl. No. 17/538,911, filed Nov. 30, 2021 Advisory Action dated Nov. 22, 2023.
U.S. Appl. No. 17/538,911, filed Nov. 30, 2021 Notice of Allowance dated Mar. 14, 2024.
U.S. Appl. No. 17/538,943, filed Nov. 30, 2021 Non-Final Office Action dated Jan. 30, 2024.
U.S. Appl. No. 17/684,180, filed Mar. 1, 2022 Advisory Action dated Apr. 4, 2024.
U.S. Appl. No. 17/684,180, filed Mar. 1, 2022 Final Office Action dated Jan. 18, 2024.
U.S. Appl. No. 17/722,151, filed Apr. 15, 2022 Advisory Action dated Jan. 2, 2024.
U.S. Appl. No. 17/722,151, filed Apr. 15, 2022 Final Office Action dated Nov. 6, 2023.
U.S. Appl. No. 17/722,151, filed Apr. 15, 2022 Non-Final Office Action dated Mar. 25, 2024.
U.S. Appl. No. 17/894,460, filed Aug. 24, 2022 Advisory Action dated Apr. 4, 2024.
U.S. Appl. No. 17/894,460, filed Aug. 24, 2022 Final Office Action dated Jan. 31, 2024.

(56) References Cited

OTHER PUBLICATIONS

U.S. Appl. No. 17/894,460, filed Aug. 24, 2022 Non-Final Office Action dated Nov. 6, 2023.
U.S. Appl. No. 18/238,281, filed Aug. 25, 2023 Non-Final Office Action dated Mar. 22, 2024.
Thermographic venous blood flow characterization with external cooling stimulation (Year: 2018).
U.S. Appl. No. 17/534,099, filed Nov. 23, 2021 Notice of Allowance dated Sep. 18, 2024.
U.S. Appl. No. 17/538,943, filed Nov. 30, 2021 Notice of Allowance dated Aug. 14, 2024.
U.S. Appl. No. 17/684,180, filed Mar. 1, 2022 Final Office Action dated Sep. 23, 2024.
U.S. Appl. No. 17/722,151, filed Apr. 15, 2022 Final Office Action dated Sep. 20, 2024.
U.S. Appl. No. 17/894,460, filed Aug. 24, 2022 Non-Final Office Action dated Sep. 25, 2024.
U.S. Appl. No. 17/979,564, filed Nov. 2, 2022 Final Office Action dated Oct. 18, 2024.
U.S. Appl. No. 17/979,601, filed Nov. 2, 2022 Non-Final Office Action dated Aug. 20, 2024.
U.S. Appl. No. 17/987,698, filed Nov. 15, 2022 Non-Final Office Action dated Sep. 20, 2024.
U.S. Appl. No. 17/684,180, filed Mar. 1, 2022 Non-Final Office Action dated May 8, 2024.
U.S. Appl. No. 17/979,564, filed Nov. 2, 2022 Non-Final Office Action dated Jun. 5, 2024.
U.S. Appl. No. 18/238,281, filed Aug. 25, 2023 Notice of Allowance dated Jul. 16, 2024.
PCT/US2022/045372 filed Sep. 30, 2022 International Search Report and Written Opinion dated Jan. 14, 2023.
PCT/US2024/037647 filed Jul. 11, 2024 International Search Report and Written Opinion dated Oct. 16, 2024.
U.S. Appl. No. 17/471,015, filed Sep. 9, 2021 Notice of Allowance dated Oct. 29, 2024.
U.S. Appl. No. 17/957,562, filed Sep. 30, 2022 Final Office Action dated Nov. 27, 2024.
U.S. Appl. No. 17/957,562, filed Sep. 30, 2022 Non-Final Office Action dated Jun. 20, 2024.
U.S. Appl. No. 17/979,601, filed Nov. 2, 2022 Final Office Action dated Dec. 5, 2024.
U.S. Appl. No. 18/113,003, filed Feb. 22, 2023 Non-Final Office Action dated Nov. 27, 2024.
US 17/684,180 filed Mar. 1, 2022 Advisory Action dated Dec. 27, 2024.
U.S. Appl. No. 17/722,151 filed Apr. 15, 2022 Advisory Action dated Dec. 27, 2024.
U.S. Appl. No. 17/894,460, filed Aug. 24, 2022 Final Office Action dated Dec. 31, 2024.
U.S. Appl. No. 17/973,171 filed Oct. 25, 2022 Non-Final Office Action dated Dec. 6, 2024.
U.S. Appl. No. 17/987,698, filed Nov. 15, 2022 Final Office Action dated Dec. 13, 2024.
U.S. Appl. No. 18/121,802, filed Mar. 15, 2023 Non-Final Office Action dated Dec. 16, 2024.
U.S. Appl. No. 18/674,601, filed May 24, 2024 Non-Final Office Action dated Jan. 7, 2025.

\* cited by examiner

ULTRASOUND IMAGING SYSTEM HAVING NEAR-INFRARED/INFRARED DETECTION

PRIORITY

This application claims the benefit of priority to U.S. Provisional Application No. 63/175,475, filed Apr. 15, 2021, which is incorporated by reference in its entirety into this application.

BACKGROUND

Readily accessing a blood vessel can require multiple sticks to access the correct blood vessel. Clinicians may use vein visualizers, medical devices that detect subcutaneous blood vessels and project a depiction of the vein topography on the skin surface, to readily access the correct blood vessel. Vein visualizers must be held some distance away from the skin surface where hands or other medical devices may disturb the depiction of the vein topography, adding difficulty to accessing the correct blood vessel. It would be beneficial to clinicians and patients to have a vein visualizer whose depiction would not be disturbed, allowing clinicians ready access to the correct blood vessel. Disclosed herein are an ultrasound imaging system and method of use that address the foregoing.

SUMMARY

Disclosed herein is an ultrasound imaging system including an ultrasound probe and a blood vessel visualization device. The ultrasound probe includes an ultrasound generation device and is configured to detect one or more blood vessels. The blood vessel visualization device is configured to project a depiction of the blood vessel topography within a target area, the blood vessel visualization device includes one or more near-infrared/infrared emitters configured to generate infrared/near-infrared waves within the target area, one or more near-infrared/infrared sensors configured to detect the difference in reflective properties of tissue and blood vessels within the target area, and one or more visual light projectors configured to project a blood vessel visualization depiction of the blood vessel topography onto the target area.

In some embodiments, the one or more visual light projectors project the blood vessel visualization depiction to one side of the ultrasound probe onto the target area.

In some embodiments, each of the one or more near-infrared sensors, the one or more near-infrared/infrared emitters, and the one or more visual light projectors are coupled to the ultrasound probe.

In some embodiments, the one or more near-infrared/infrared emitters and the one or more near-infrared/infrared sensors are located oblique to an ultrasound acoustic stack of the ultrasound probe.

In some embodiments, the blood vessel visualization device includes a console having non-transitory computer readable medium, an energy source and a plurality of logic modules.

In some embodiments, the console is in communication with each of the ultrasound probe, the one or more near-infrared/infrared emitters, the one or more near-infrared/infrared sensors and the one or more visual light projectors.

In some embodiments, the energy source is in communication with each of the one or more infrared/near-infrared emitters, the one or more infrared/near-infrared sensors, and the one or more visual light projectors.

In some embodiments, the energy source is untethered to one or more of the one or more near-infrared/infrared emitters, the one or more near-infrared/infrared sensors, or the one or more visible light projectors.

In some embodiments, the energy source includes an induction coupling system configured to wirelessly provide energy to the one or more near-infrared/infrared emitters, the one or more near-infrared/infrared sensors or the one or more visible light projectors.

In some embodiments, the energy source is tethered to one or more of the infrared/near-infrared emitters, the infrared/near-infrared sensors or the visible light projectors.

In some embodiments, the plurality of logic modules, when executed by the processor, are configured to perform operations including receiving ultrasound data from the ultrasound probe, correlating a detected location of one or more blood vessels with a starting location for a blood vessel visualization depiction within the target area, activating each of the near-infrared/infrared emitters, the near-infrared/infrared sensors, and the visual light projectors, receiving detected near-infrared/infrared data from the near-infrared/infrared sensors, and generating and projecting to one side of the ultrasound probe, the blood vessel visualization depiction within the target area.

In some embodiments, the ultrasound generation device includes a microelectromechanical systems based device.

In some embodiments, the ultrasound probe includes the ultrasound generation device, the one or more near-infrared/infrared sensors and the one or more visual light projectors, and a vascular access device includes the one or more near-infrared/infrared emitters, the vascular access device configured to be inserted into one of the detected blood vessels within the target area.

In some embodiments, the vascular access device includes a visual indicator configured to be activated based upon a vascular access device trajectory relative to a target blood vessel or an identified blood vessel type including an artery or a vein.

Also disclosed herein is a method of detecting one or more blood vessels in a target area and generating and projecting a blood vessel visualization depiction over the target area. The method includes detecting, by ultrasound and near-infrared/infrared electromagnetic waves, blood vessel topography in the target area, generating a blood vessel visualization depiction, and projecting, to one side of an ultrasound probe, the blood vessel visualization depiction on the target area.

In some embodiments, detecting by near-infrared/infrared electromagnetic waves includes one or more near-infrared/infrared sensors detecting a difference in reflective properties of tissue and blood vessels within the target area.

In some embodiments, detecting by near-infrared/infrared electromagnetic waves includes the electromagnetic waves being emitted from one or more near-infrared/infrared emitters coupled to the ultrasound probe and being detected by the one or more near-infrared/infrared sensors coupled to the ultrasound probe.

In some embodiments, detecting by near-infrared/infrared electromagnetic waves includes the electromagnetic waves being emitted from one or more near-infrared/infrared emitters coupled to a vascular access device and being detected by one or more near-infrared/infrared sensors coupled to the ultrasound probe.

In some embodiments, generating a blood vessel visualization depiction includes a console in communication with each of the ultrasound probe, the one or more near-infrared/infrared emitters and the near-infrared/infrared sensors generating the blood vessel visualization depiction using ultrasound data received from the ultrasound probe and electromagnetic wave data received from the one or more near-infrared/infrared sensors.

In some embodiments, projecting, to one side of an ultrasound probe, the blood vessel visualization depiction on the target area includes one or more visual light projectors coupled to the ultrasound probe projecting the blood vessel visualization depiction onto the target area.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
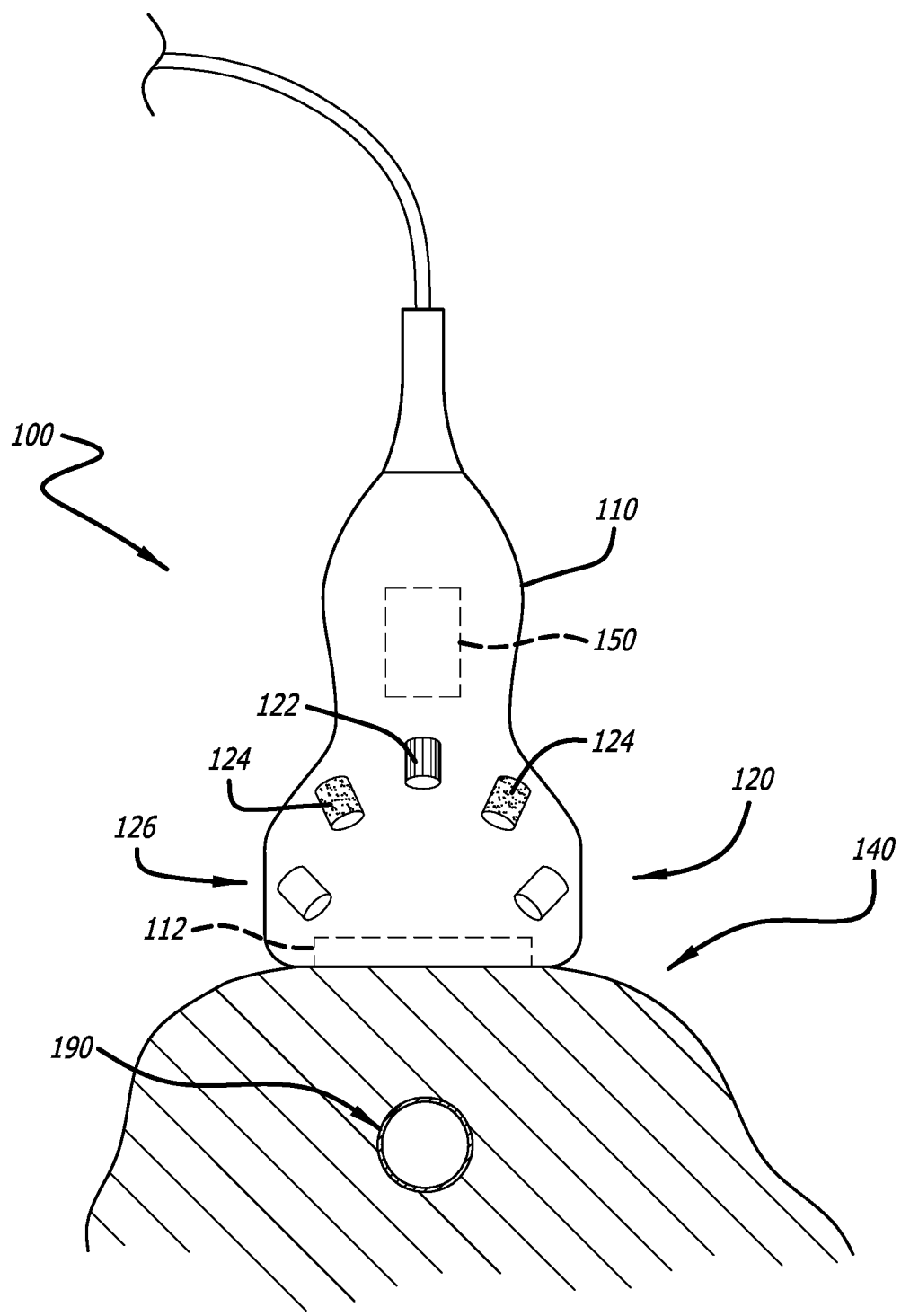
FIG. 1 illustrates a cross sectional view of an ultrasound imaging system including an ultrasound probe having a blood vessel visualization device coupled thereto, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Unless defined otherwise, all technical and scientific terms used herein have the same meaning as commonly understood by those of ordinary skill in the art.

FIG. 1 illustrates a perspective view of an ultrasound imaging system ("system") 100 including an ultrasound probe 110 having a blood vessel visualization device 120 coupled thereto, in accordance with some embodiments. In some embodiments, the ultrasound probe 110 may be configured to detect one or more blood vessels within a target area 140 by contacting a skin surface within the target area 140. In some embodiments, the ultrasound probe 110 may include an ultrasound generation device 112 including an ultrasound acoustic stack or other various modalities of ultrasound generation (e.g., microelectromechanical systems (MEMS) based, etc.). In some embodiments, the target area 140 may include the one or more blood vessels 190 to be accessed by a vascular access device. The blood vessel visualization device 120 may be configured to sense subcutaneous blood vessel topography and project, to one side of the ultrasound probe 110, a depiction of the sensed blood vessel topography on the skin surface of the target area 140, allowing a clinician to access a blood vessel without disturbing the depiction.

In some embodiments, the blood vessel visualization device 120 includes one or more near-infrared/infrared ("NIR/IR") sensors 122, one or more NIR/IR emitters 124, and one or more visual light projectors 126. The NIR/IR sensors 122, the NIR/IR emitters 124 and the visual light projectors 126 may all be in communication with a console 150. In some embodiments, the NIR/IR sensors 122, the NIR/IR emitters 124 and the visual light projectors 126 may be in wireless communication with the console 150. In some embodiments, the console 150 may be in communication with the ultrasound probe 110 including in communication with the ultrasound generation device 112. In some embodiments, the console 150 may be coupled to the ultrasound probe 110 or integrated into the ultrasound probe 110. In some embodiments, the NIR/IR emitters 124 may be configured to emit electromagnetic waves within the near-infrared/infrared spectrum within the target area 140. The electromagnetic waves reflect off of subcutaneous structures such as blood vessels. In some embodiments, the NIR/IR sensors 122 may be configured to detect the reflected NIR/IR electromagnetic waves and transmit the detected NIR/IR data to the console 150. In some embodiments, the NIR/IR sensors 122 may be configured to detect the difference in reflective properties of tissue and blood vessels within the target area 140. The console 150 may be configured to receive the detected NIR/IR data, correlate the difference in electromagnetic reflectance between blood vessels and surrounding tissues to generate a blood vessel visualization depiction. The one or more visual light projectors 126 may be configured to project the blood vessel visualization depiction to one side of the ultrasound probe 110 on the skin surface within the target area 140. In some embodiments, the NIR/IR emitters 124 and the NIR/IR sensors 122 may be located oblique to the ultrasound acoustic stack 112.

Figure 2:
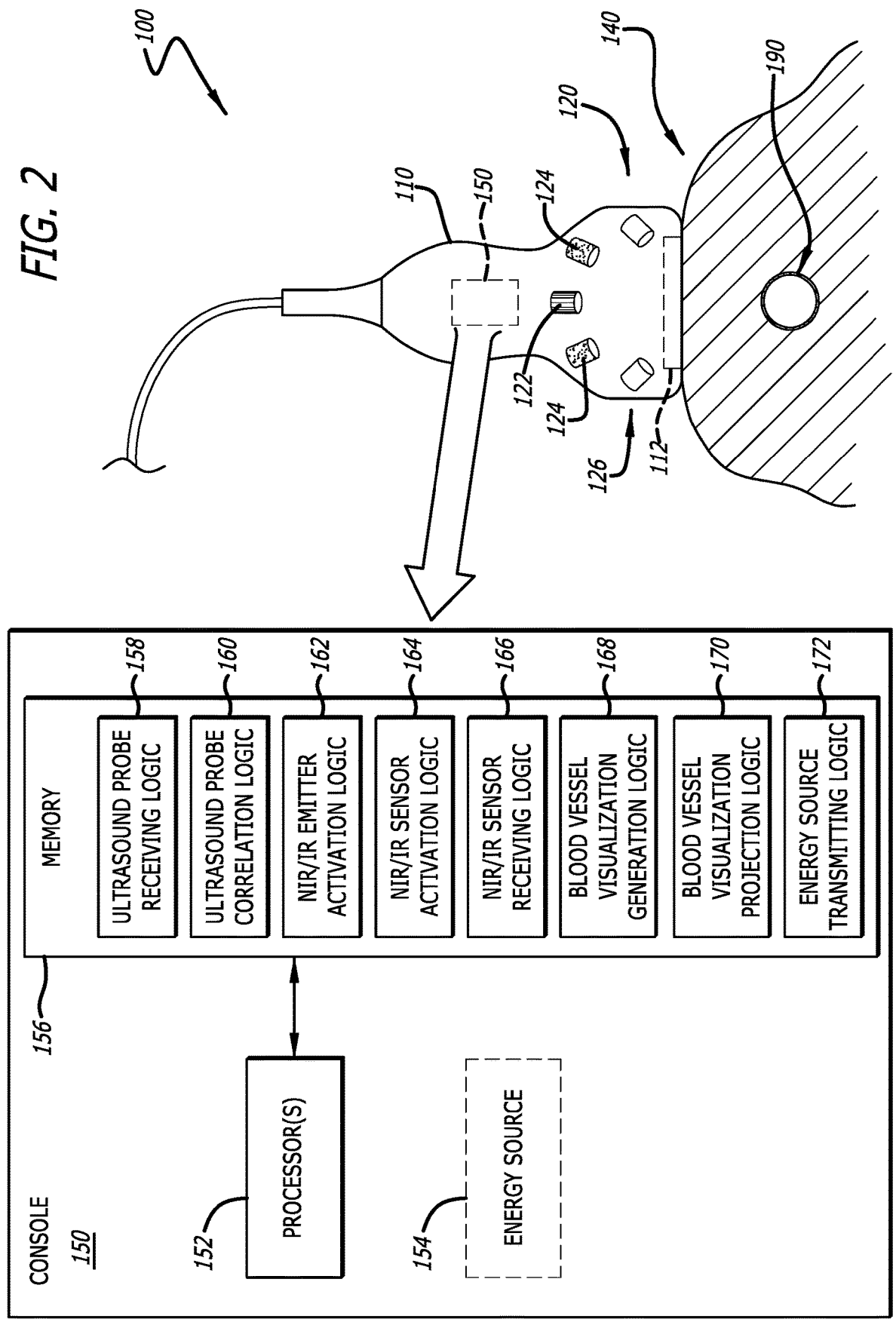
FIG. 2 illustrates a block diagram of some components of the ultrasound imaging system including the ultrasound probe having a console, in accordance with some embodiments.

FIG. 2 illustrates a block diagram of some components of the ultrasound imaging system 100 including the console 150, in accordance with some embodiments. In some embodiments, the console 150 may be coupled to or integrated into the ultrasound probe 110. In some embodiments, the console 150 may be in communication with the ultrasound probe 110 and be configured to receive the ultrasound data to generate a portion of the blood vessel visualization depiction within the target area 140. The blood vessel visualization device 120 may include the console 150 in communication with each of: the one or more blood vessel sensors 122, the one or more blood vessel emitters 124, the visible light projectors 126 and the ultrasound probe 110. In some embodiments, the console 150 may be in wireless communication with each of the blood vessel sensors 122, the blood vessel emitters 124, the visible light projectors 126 and the ultrasound probe 110. Exemplary wireless communication modalities can include WiFi, Bluetooth, Near Field Communications (NFC), cellular Global System for Mobile Communication ("GSM"), electromagnetic (EM), radio frequency (RF), combinations thereof, or the like.

In some embodiments, the console 150 may include one or more processors 152, an energy source 154, non-transitory computer readable medium ("memory") 156 and a plurality of logic modules. The plurality of logic modules may include one or more of: a ultrasound probe receiving logic 158, a ultrasound probe correlation logic 160, a NIR/IR sensor activation logic 162, a NIR/IR emitter activation logic 164, a NIR/IR sensor receiving logic 166, a blood vessel visualization generation logic 168, a blood vessel visualization projection logic 170 and an energy source transmitting logic 172. In some embodiments, the ultrasound probe receiving logic 158 may be configured to receive the ultrasound wave data from the ultrasound probe 110 including from the ultrasound generation device 112. In some embodiments, the ultrasound probe correlation logic 160 may be configured to correlate the detected location of the one or more blood vessels 190 with a starting location for the blood vessel visualization depiction within the target area 140. In some embodiments, the NIR/IR emitter activation logic 164 may be configured to activate the NIR/IR emitters 124 to emit electromagnetic waves within the target area 140. In some embodiments, the NIR/IR sensor activation logic 162 may be configured to activate the NIR/IR sensors 122. In some embodiments, the NIR/IR sensor receiving logic 166 may be configured to detect the reflected electromagnetic waves within the target area 140. In some embodiments, the NIR/IR sensor receiving logic 166 may be configured to detect the difference in the reflective properties of tissue and blood vessels 190 within the target area 140. In some embodiments, the blood vessel visualization generation logic 168 may be configured to generate the blood vessel visualization depiction. The blood vessel visualization generation logic 168 may be configured to receive the detected electromagnetic wave data and the detected ultrasound wave data to generate the blood vessel visualization depiction of the blood vessels 190 within the target area 140. In some embodiments, the blood vessel visualization depiction of the blood vessels 190 within the target area 140 may include a topographical map depicting the blood vessels 190 and surrounding tissues. In some embodiments, the blood vessel visualization projection logic 170 may be configured to use the one or more visible light projectors 126 to project the blood vessel visualization depiction on the target area 140.

In some embodiments, the energy source 154 may be configured to provide power to the one or more NIR/IR emitters 124, the one or more NIR/IR sensors 122 and the one or more visible light projectors 126. In some embodiments, the NIR/IR emitters 124, the NIR/IR sensors 122, or the visible light projectors 126 may be tethered to the energy source 154. In some embodiments, the energy source 154 may be in communication with one or more of the NIR/IR sensors 122, the NIR/IR emitters 124 and the visible light projectors 126. In some embodiments, the energy source 154 may include a battery coupled to one or more of the NIR/IR emitters 124, the NIR/IR sensors 122 and the visible light projectors 126. In some embodiments, the NIR/IR sensors 122 or the NIR/IR emitters 124 may be untethered to the ultrasound probe 110 [e.g., coupled to a vascular access device 180 (see FIG. 3)]. The energy source 154 may then be configured to wirelessly provide power to either the NIR/IR sensors 122 or the NIR/IR emitters 124. The energy source 154 may be configured to wirelessly provide power to the NIR/IR sensors 122 through an induction coupling system. In this embodiment, the plurality of logic modules may be configured to include an energy source transmitting logic 172 configured to regulate the amount of power that is wirelessly provided to the NIR/IR sensors 122 or NIR/IR emitters 124.

Figure 3:
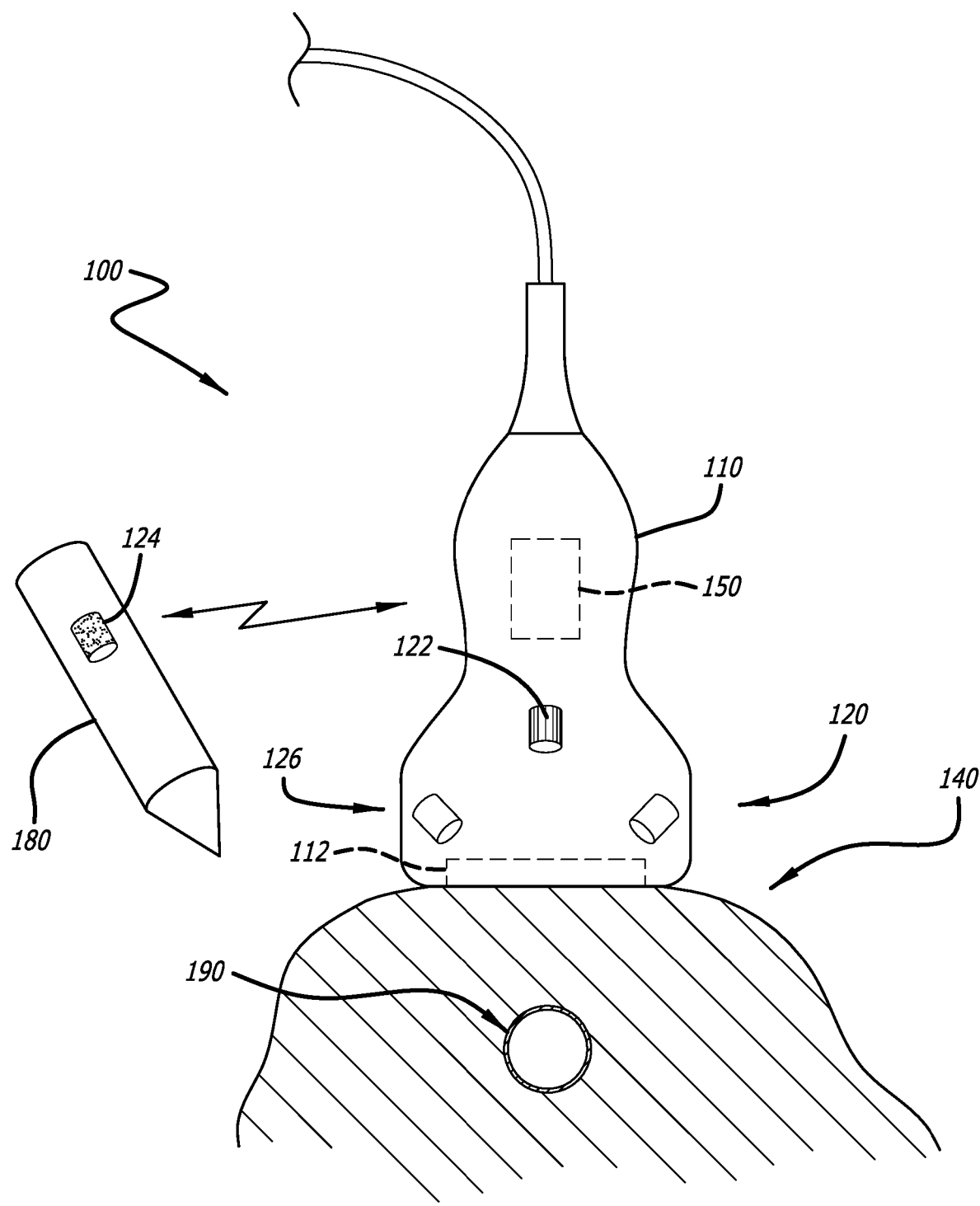
FIG. 3 illustrates a cross sectional view of the ultrasound imaging system including the ultrasound probe and a vascular access device, in accordance with some embodiments.

FIG. 3 illustrates a cross sectional view of the ultrasound imaging system 100 wherein the NIR/IR emitters 124 are coupled to a vascular access device 180 and the NIR/IR sensors 122 and visual light projectors 126 are coupled to the ultrasound probe 110. As used herein a "vascular access device" can include a catheter, peripherally inserted central catheter ("PICC"), peripheral intravenous line ("PIV"), central venous catheter ("CVC"), midline catheter, a needle, or the like. In some embodiments, the NIR/IR emitters 124 and the NIR/IR sensors 122 may be separated between the ultrasound probe 110 and the vascular access device 180. In some embodiments, the NIR/IR emitters 124 may be coupled to the vascular access device 180 and the NIR/IR sensors 122 may be coupled to the ultrasound probe 110. In some embodiments, the NIR/IR emitters 124 may be coupled to the ultrasound probe 110 and the NIR/IR sensors 122 may be coupled to the vascular access device 180. In some embodiments, the NIR/IR emitters 124 may be integrated into the vascular access device 180. In this embodiment, wherein either the NIR/IR emitters 124 or the NIR/IR sensors 122 are coupled to the vascular access device 180, the NIR/IR emitters or NIR/IR sensors 122 may be powered through induction coupling. In an embodiment, the vascular access device 180 is enabled with a visual indicator, wherein the visual indicator is activated based upon the trajectory of the vascular access device 180 relative to a target blood vessel or the visual indicator is activated based upon the identified blood vessel type. The console 150 functions as described above.

Figure 4C:
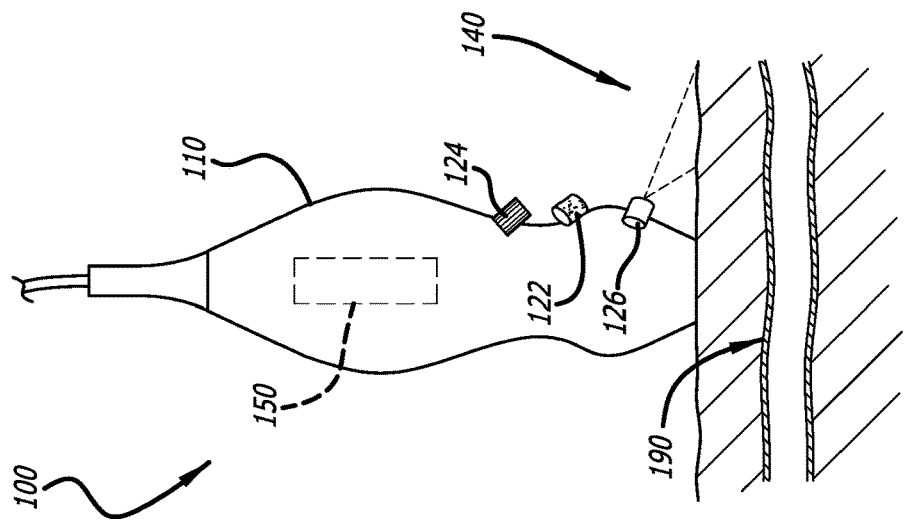
FIGS. 4A-4C illustrate a side cross-sectional view of an exemplary method of generating and projecting a blood vessel visualization depiction over a target area, in accordance with some embodiments.
Figure 4B:
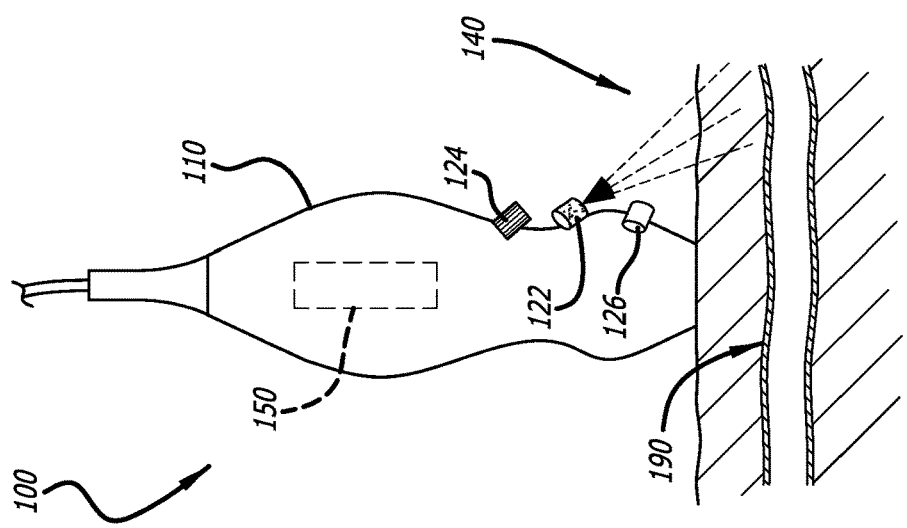
Figure 4A:
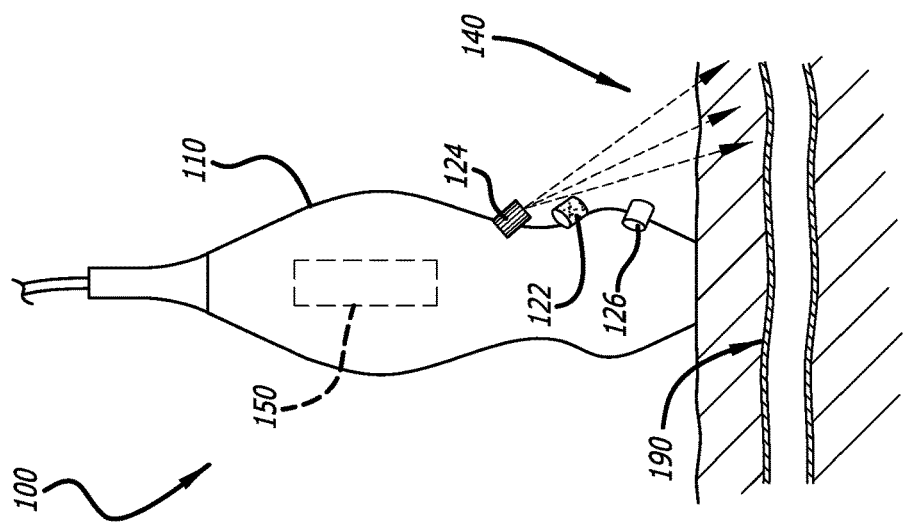

FIGS. 4A-4C illustrates a side cross-sectional view of an exemplary method of detecting blood vessel topography and projecting a blood vessel visualization depiction over the target area 140, in accordance with some embodiments. The ultrasound probe 110 includes the NIR/IR emitters 124, the NIR/IR sensors 122 and the visual light projectors 126, as described above. As illustrated in FIG. 4A, in some embodiments, the ultrasound imaging system 100 including the ultrasound probe 110 may be configured to detect one or more blood vessels 190 within the target area 140. In some embodiments, the ultrasound probe 110 may be configured to detect the one or more blood vessels 190 within target area 140 by ultrasound. The NIR/IR emitters 124 may emit electromagnetic waves subcutaneously within the target area 140. As illustrated in FIG. 4A, in some embodiments, the NIR/IR emitters 124, the NIR/IR sensors 122, and the visual light projectors 126 may be arranged in various configurations on the ultrasound probe 110. In some embodiments, the NIR/IR emitters 124 may be located above the NIR/IR sensors 122, and the NIR/IR sensors 122 may be located above the visual light projectors 126. In some embodiments, the NIR/IR emitters 124 may be located adjacent to the NIR/IR sensors 122. In some embodiments, the visual light projectors 126 may be located adjacent to the NIR/IR sensors 122 or the NIR/IR emitters 124.

As illustrated in FIG. 4B, the NIR/IR sensors 122 may be configured to detect the reflected electromagnetic waves, including the difference in reflective properties of the tissue and blood vessels within the target area 140. The NIR/IR sensors 122 may transmit the detected electromagnetic waves to the console 150 where the console 150 may use the detected electromagnetic wave data, along with the detected blood vessel data within the target area 140 to generate a blood vessel visualization depiction. As illustrated in FIG. 4C, the visual light projectors 126 may be configured to receive the blood vessel visualization depiction and project the blood vessel visualization depiction onto the target area 140 including onto a skin surface. A user may use the blood vessel visualization depiction to accurately access the blood vessel 190 within the target area 140.

Figure 5:
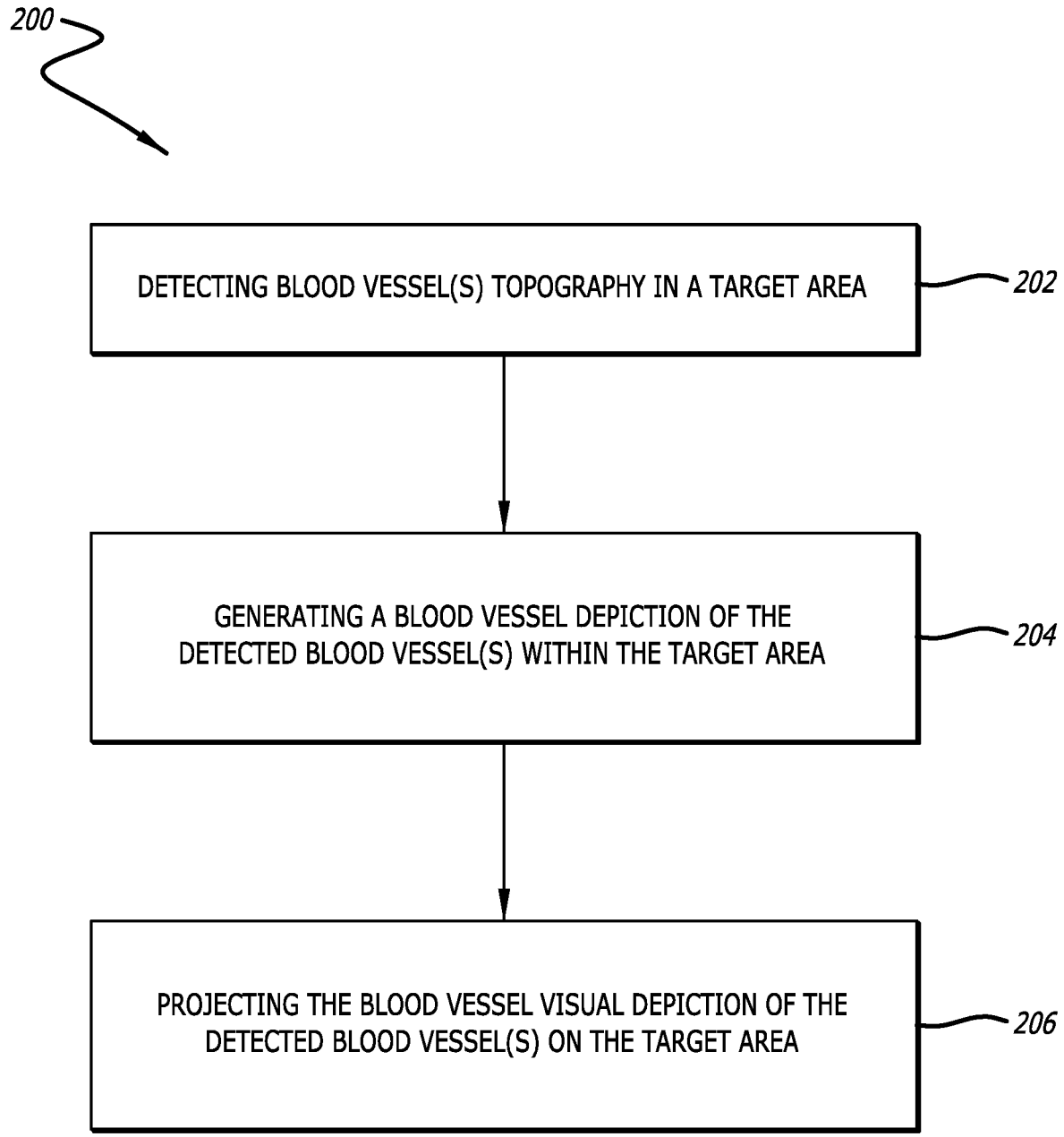
FIG. 5 illustrates a flow chart of an exemplary method of detecting one or more blood vessels in a target are, generating and projecting a blood vessel visualization depiction over the target area, in accordance with some embodiments.

FIG. 5 illustrates a flow chart of the method 200 of detecting one or more blood vessels 190 in a target area 140 and generating and projecting a blood vessel visualization depiction over the target area 140, in accordance with some embodiments. In some embodiments, the method 200 includes detecting blood vessel topography in a target area 140 (block 202). In some embodiments, detecting blood vessel topography in the target area 140 includes detecting, by near-infrared/infrared electromagnetic waves, blood vessel topography in the target area 140. In some embodiments, detecting blood vessel topography in the target area 140 includes detecting, by ultrasound, blood vessel topography in the target area 140. In some embodiments, detecting blood vessel topography in the target area 140 includes detecting by ultrasound and near-infrared/infrared electromagnetic waves, blood vessel topography in the target area 140. In some embodiments, detecting blood vessel topography includes using the NIR/IR emitters 124 configured to emit near-infrared/infrared electromagnetic waves and NIR/IR sensors 122 coupled to the ultrasound probe 110 configured to detect the near-infrared/infrared electromagnetic waves to detect the blood vessel topography. In some embodiments, detecting blood vessel topography includes using the NIR/IR emitters 124 couped to the vascular access device 180 configured to emit near-infrared/infrared electromagnetic waves and the NIR/IR sensors 122 coupled to the ultrasound probe 110 configured to detect the near-infrared/infrared electromagnetic waves to detect the blood vessel topography. In some embodiments, detecting blood vessel topography in the target area 140 includes the NIR/IR sensors 122 detecting the difference in reflective properties of tissue and blood vessels within the target area 140. The method 200 further includes generating a blood vessel visual depiction of the detected blood vessels 190 within the target area 140 (block 204). In some embodiments, generating the blood vessel visual depiction includes the console 150 generating the blood vessel visual depiction. In some embodiments, the console 150 may use blood vessel topography data received from the NIR/IR sensors 122 to generate the blood vessel visual depiction. In some embodiments, the console 150 may also use ultrasound data received from the ultrasound probe 110 to generate the blood vessel visual depiction. In some embodiments, the method 200 includes projecting, to one side of the ultrasound probe 110, the blood vessel visual depiction of the detected blood vessel on the target area 140 (block 206). In some embodiments projecting the blood vessel visual depiction of the detected blood vessels on the target area 140 includes the blood vessel visual depiction having distinct colors indicating different blood vessel type (e.g., artery versus vein).

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound imaging system, comprising:
an ultrasound probe configured to detect one or more blood vessels, the ultrasound probe including an ultrasound generation device defining a bottom side of the ultrasound probe; and
a blood vessel visualization device, the blood vessel visualization device configured to project a depiction of blood vessel topography within a target area, the blood vessel visualization device including:
one or more near-infrared/infrared emitters configured to generate infrared/near-infrared waves within the target area;
one or more near-infrared/infrared sensors configured to detect a difference in reflective properties of tissue and blood vessels within the target area; and
one or more visual light projectors configured to project a blood vessel visualization depiction of the blood vessel topography onto the target area, wherein each of the one or more near-infrared/infrared sensors, the one or more near-infrared/infrared emitters, and the one or more visual light projectors are:
directly coupled to the ultrasound probe, and
arranged on a front side of the ultrasound probe, the front side extending upward away from the bottom side in a substantially perpendicular direction with respect to the bottom side.

2. The ultrasound imaging system according to claim 1, wherein the one or more visual light projectors project the blood vessel visualization depiction to one side of the ultrasound probe onto the target area.

3. The ultrasound imaging system according to claim 1, wherein the one or more near-infrared/infrared emitters and the one or more near-infrared/infrared sensors are located oblique to an ultrasound acoustic stack of the ultrasound probe.

4. The ultrasound imaging system according to claim 1, wherein the blood vessel visualization device includes a console having non-transitory computer readable medium, an energy source and a plurality of logic modules.

5. The ultrasound imaging system according to claim 4, wherein the console is in communication with each of the ultrasound probe, the one or more near-infrared/infrared emitters, the one or more near-infrared/infrared sensors and the one or more visual light projectors.

6. The ultrasound imaging system according to claim 5, wherein the energy source is in communication with each of the one or more near-infrared/infrared emitters, the one or more near-infrared/infrared sensors, and the one or more visual light projectors.

7. The ultrasound imaging system according to claim 6, wherein the energy source is untethered to one or more of the one or more near-infrared/infrared emitters, the one or more near-infrared/infrared sensors, or the one or more visible light projectors.

8. The ultrasound imaging system according to claim 6, wherein the energy source includes an induction coupling system configured to wirelessly provide energy to the one or more near-infrared/infrared emitters, the one or more near-infrared/infrared sensors or the one or more visible light projectors.

9. The ultrasound imaging system according to claim 6, wherein the energy source is tethered to the one or more near-infrared/infrared emitters, the one or more near-infrared/infrared sensors or the one or more visible light projectors.

10. The ultrasound imaging system according to claim 4, wherein the plurality of logic modules, when executed by one or more processors, are configured to perform operations:
receiving ultrasound data from the ultrasound probe;
correlating a detected location of the one or more blood vessels with a starting location for the blood vessel visualization depiction within the target area;
activating each of the one or more near-infrared/infrared emitters, the one or more near-infrared/infrared sensors, and the one or more visual light projectors;
receiving detected near-infrared/infrared data from the one or more near-infrared/infrared sensors; and
generating and projecting to one side of the ultrasound probe, the blood vessel visualization depiction within the target area.

11. The ultrasound imaging system according to claim 1, wherein the ultrasound generation device includes a microelectromechanical systems based device.

12. The ultrasound imaging system according to claim 1, wherein a vascular access device includes a visual indicator configured to be activated based upon a vascular access device trajectory relative to a target blood vessel or an identified blood vessel type including an artery or a vein.

13. A method of detecting one or more blood vessels in a target area and generating and projecting a blood vessel visualization depiction over the target area, comprising:
detecting, by ultrasound and near-infrared/infrared electromagnetic waves, blood vessel topography in the target area, wherein detecting by near-infrared/infrared electromagnetic waves includes the electromagnetic waves being emitted from one or more near-infrared/infrared emitters directly coupled to an ultrasound probe and being detected by one or more near-infrared/infrared sensors directly coupled to the ultrasound probe;
generating the blood vessel visualization depiction; and
projecting to one side of an ultrasound probe, the blood vessel visualization depiction on the target area,
wherein:
the ultrasound probe includes an ultrasound generation device defining a bottom side of the ultrasound probe, and
each of the one or more near-infrared/infrared sensors and the one or more near-infrared/infrared emitters are arranged on a front side of the ultrasound probe, the front side extending upward away from the bottom side in a substantially perpendicular direction with respect to the bottom side.

14. The method according to claim 13, wherein detecting by near-infrared/infrared electromagnetic waves includes the one or more near-infrared/infrared sensors detecting a difference in reflective properties of tissue and blood vessels within the target area.

15. The method according to claim 14, wherein generating the blood vessel visualization depiction includes a console in communication with each of the ultrasound probe, the one or more near-infrared/infrared emitters and the one or more near-infrared/infrared sensors generating the blood vessel visualization depiction using ultrasound data received from the ultrasound probe and electromagnetic wave data received from the one or more near-infrared/infrared sensors.

16. The method according to claim 15, wherein projecting to one side of the ultrasound probe, the blood vessel visualization depiction on the target area includes one or more visual light projectors coupled to the ultrasound probe projecting the blood vessel visualization depiction onto the target area.

* * * * *